(12) United States Patent  (10) Patent No.: US 9,078,592 B2
Jiang et al.  (45) Date of Patent: Jul. 14, 2015

(54) ULTRASONIC STRAIN IMAGING DEVICE WITH SELECTABLE COST-FUNCTION

(75) Inventors: Jingfeng Jiang, Madison, WI (US); Timothy J. Hall, Madison, WI (US)

(73) Assignee: Wisconsin Alumni Research Foundation, Madison, WI (US)

( * ) Notice: Subject to any disclaimer, the term of this patent is extended or adjusted under 35 U.S.C. 154(b) by 894 days.

(21) Appl. No.: 12/258,532

(22) Filed: Oct. 27, 2008

(65) Prior Publication Data

US 2010/0106018 A1  Apr. 29, 2010

(51) Int. Cl.
*A61B 8/00* (2006.01)
*A61B 8/08* (2006.01)

(52) U.S. Cl.
CPC .. *A61B 8/08* (2013.01); *A61B 8/485* (2013.01)

(58) Field of Classification Search
CPC .................................. A61B 8/485; A61B 8/08
USPC ......... 600/438, 437, 440, 442, 443, 449, 450, 600/459; 382/128, 173; 73/570
See application file for complete search history.

(56) References Cited

U.S. PATENT DOCUMENTS

| | | | | |
|---|---|---|---|---|
| 6,270,459 | B1 * | 8/2001 | Konofagou et al. | 600/449 |
| 6,277,074 | B1 * | 8/2001 | Chaturvedi et al. | 600/437 |
| 6,447,450 | B1 * | 9/2002 | Olstad | 600/437 |
| 6,508,768 | B1 * | 1/2003 | Hall et al. | 600/443 |
| 6,527,717 | B1 * | 3/2003 | Jackson et al. | 600/437 |
| 6,558,324 | B1 * | 5/2003 | Von Behren et al. | 600/440 |
| 6,875,176 | B2 * | 4/2005 | Mourad et al. | 600/442 |
| 6,941,196 | B1 * | 9/2005 | Garypie et al. | 701/21 |
| 6,976,961 | B2 * | 12/2005 | Jackson et al. | 600/443 |
| 6,994,673 | B2 * | 2/2006 | Lysyansky et al. | 600/443 |
| 7,033,320 | B2 * | 4/2006 | Von Behren et al. | 600/443 |
| 7,225,013 | B2 * | 5/2007 | Geva et al. | 600/513 |
| 7,303,530 | B2 * | 12/2007 | Barnes et al. | 600/459 |
| 7,632,231 | B2 * | 12/2009 | Jiang et al. | 600/437 |
| 7,678,051 | B2 * | 3/2010 | Fan et al. | 600/438 |
| 7,738,683 | B2 * | 6/2010 | Cahill et al. | 382/128 |
| 7,846,098 | B2 * | 12/2010 | Bakircioglu et al. | 600/440 |
| 7,995,810 | B2 * | 8/2011 | Li et al. | 382/128 |
| 2003/0202594 | A1 * | 10/2003 | Lainema | 375/240.16 |
| 2006/0018548 | A1 * | 1/2006 | Chen et al. | 382/190 |
| 2006/0079781 | A1 * | 4/2006 | Germond-Rouet et al. | 600/450 |
| 2006/0285731 | A1 | 12/2006 | Jiang et al. | |
| 2007/0058865 | A1 * | 3/2007 | Li et al. | 382/173 |
| 2007/0073145 | A1 * | 3/2007 | Fan et al. | 600/437 |
| 2007/0234806 | A1 * | 10/2007 | Jiang et al. | 73/570 |
| 2008/0161687 | A1 * | 7/2008 | Suri et al. | 600/437 |
| 2008/0306384 | A1 * | 12/2008 | Boctor et al. | 600/443 |
| 2010/0106018 | A1 * | 4/2010 | Jiang et al. | 600/438 |

* cited by examiner

*Primary Examiner* — Unsu Jung
*Assistant Examiner* — Serkan Akar
(74) *Attorney, Agent, or Firm* — Boyle Fredrickson, S.C.

(57) ABSTRACT

An elasticity measuring system determines tissue displacement between a pre-deformation and post-deformation image by a matching process using a cost function accepting as its arguments continuity of the tissue motion and correlation of the tissue in making the block matching. The invention allows the selection among different cost functions for different imaging situations or tissue types, to provide improved displacement calculations using a priori knowledge about the tissue and structure of tissue interfaces or information derived during the scanning process.

18 Claims, 3 Drawing Sheets

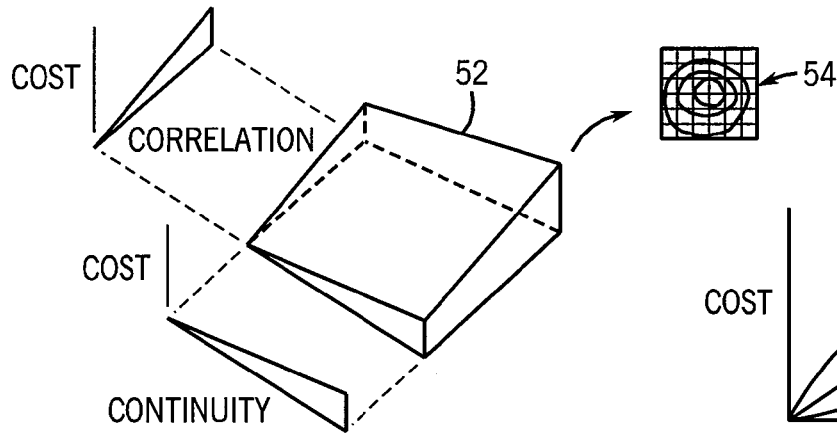
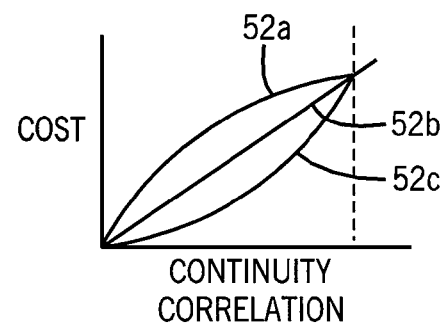
FIG. 3
FIG. 4
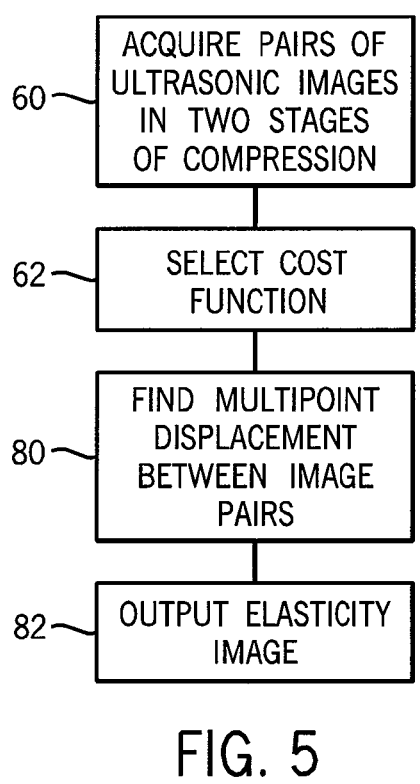
FIG. 5
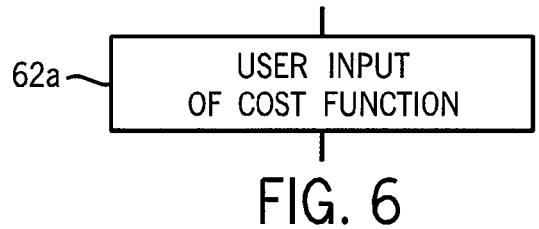
FIG. 6
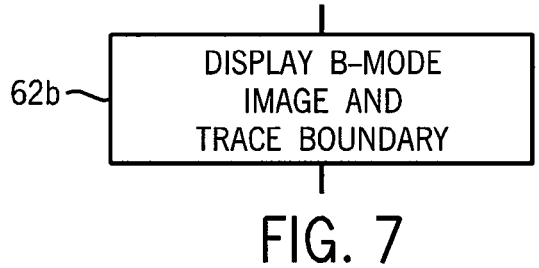
FIG. 7
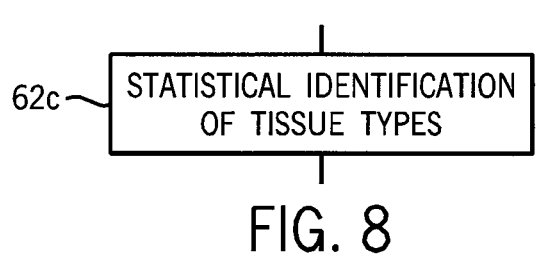
FIG. 8

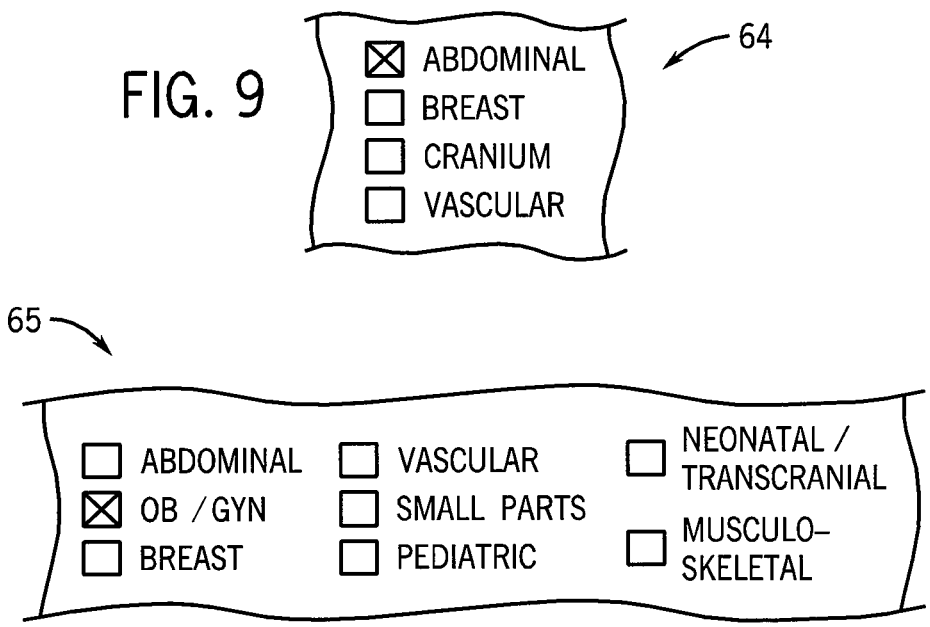
FIG. 9
FIG. 10
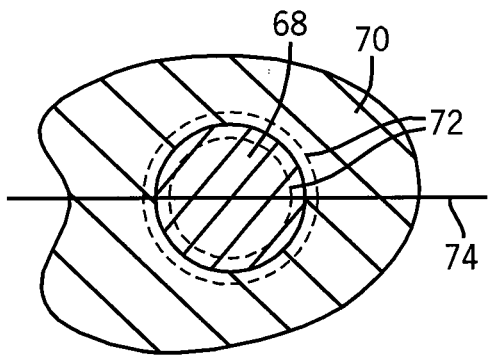
FIG. 11
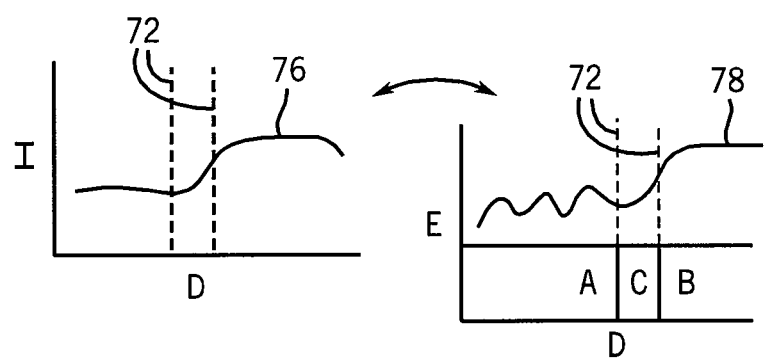
FIG. 12

ULTRASONIC STRAIN IMAGING DEVICE WITH SELECTABLE COST-FUNCTION

STATEMENT REGARDING FEDERALLY SPONSORED RESEARCH

This invention was made with United States government support awarded by the following agency: NIH CA100373. The United States government has certain rights in this invention.

CROSS-REFERENCE TO RELATED APPLICATIONS

--

BACKGROUND OF THE INVENTION

The present invention relates to ultrasonic imaging and, in particular, to an improved method and apparatus for calculating material displacement used to produce elasticity images including local strain, modulus and Poison' ratio images.

Ultrasonic elasticity imaging produces an image showing the elastic parameters of the material being measured. When used in medicine, elasticity imaging is analogous to palpation by a physician, that is, the pressing of tissue by the physician to feel differences in elasticity of underlying structures.

In a common form of elasticity imaging, two separate ultrasonic images are obtained, the first image with tissue in an undeformed state relative to the second image ("pre-deformation") and the second image with the tissue in a deformed state ("post deformation"). The two images are analyzed to deduce the amount of displacement of the tissue at corresponding areas within the images. One type of tissue elastic parameters is the local strain, i.e. the gradient in the displacement computed at many points over the image, which provides an indication of the tissue elasticity at those points. The general principles of elasticity imaging and techniques for determining displacement of the tissue between two ultrasonic images are described in detail in U.S. Pat. No. 6,508,768, hereby incorporated by reference.

An important aspect of processing the pre-deformation and post-deformation ultrasonic images to deduce the displacement of tissue elements, is identifying motion patterns of corresponding points between the two images. This is normally accomplished by identifying each point in the pre-deformation image and establishing a region of points (kernel) surrounding that identified point. This kernel is then moved within a one, two or three dimensional search window within the post-deformation image to identify the location within the search window providing the best match between the points of the kernel and a corresponding kernel in the post-deformation image.

Normally the size of the search window must be sufficient to accommodate likely tissue displacements between the pre-deformation and post-deformation images, but must also be limited to manage the computational burden of matching points with each other and to reduce the chance of possible false matches that violate a priori assumptions about limited mobility of a tissue continuum reacting to external mechanical stimuli.

SUMMARY OF THE INVENTION

The present inventors have recognized that there is an inherent tension in matching kernels of the pre-deformation and post-deformation images between restoration of signal coherence (high correlation between matching kernels) and correctness of the matching with respect to other matches (continuity or limited tissue mobility), and that this tension may best be resolved using mathematical optimization where cost functions allow different trade-offs between correlation and continuity for different tissue types and imaging situations. By allowing this trade-off to be varied, for example, based on a priori knowledge about the imaging situation, improved images may be obtained.

Specifically then, the present invention provides an ultrasound strain imaging machine having a transducer assembly producing an axial ultrasonic beam through a region of interest of a material and acquiring an echo signal from that region of interest in a first and second state of deformation. An electronic computer receives the echo signals from the transducer assembly and executes a stored program to: (i) select among cost functions providing different weighting between correlation and continuity in a matching of regions of the echo signals; (ii) apply the cost function in identifying corresponding regions of the echo signals between the first and second states to deduce displacement of the tissue under deformation; and (iii) output information to an operator revealing elastic parameters of the tissue based on the deduced displacement.

It is thus an object of at least one embodiment of the invention to vary the cost function used for matching elements of the pre-deformation and post-deformation image to better tailor the imaging process to different tissue types and imaging protocols.

The electronic computer may select among cost functions using a selection input from the user.

It is thus an object of at least one embodiment of the invention to permit the user to provide additional information about the imaging task to improve the imaging process.

The cost function selection input by the user may identify a tissue type.

It is thus an object of at least one embodiment of the invention to provide a simple and intuitive method of selecting among cost functions according to typical tissue qualities.

The tissue type is selected from the group consisting of breast, liver, cranium, thyroid, prostate, uterus and vasculature etc.

It is thus an object of at least one embodiment of the invention to provide empirically derived cost functions for common tissue types.

Alternatively, the cost function selection input by the user may be an imaging protocol such as abdominal, OB/GYN, breast, vascular, small parts, pediatric, neonatal transcranial, and musculoskeletal.

Thus, it is an object of at least one embodiment of the invention to permit the incorporation of cost function selection into systems that already allow the user to select particular imaging protocols to control other aspects of the ultrasound machine.

In an alternative embodiment, the electronic computer may select among cost functions using a B-mode image or other ultrasound-based parametric image generated from at least one of the echo signals.

It is thus an object of at least one embodiment of the invention to allow different cost functions to be applied to different portions of the image.

The electronic computer may select a cost function having reduced emphasis on correlation near boundaries between organs identified from the parametric image.

It is thus an object of at least one embodiment of the invention to relax the continuity requirements when there is a priori knowledge of a tissue interface.

The boundaries identified maybe input by a user demarcating the boundaries or the boundaries may be automatically identified by image statistics of the parametric images.

The process of applying a cost function in the motion estimation between two images may be achieved by dynamic programming techniques (e.g. Viterbi algorithm) to shorten the computational process.

It is thus an object of at least one embodiment of the invention to provide a simple but powerful way of integrating a cost function into the block matching process.

The cost function may provide cost that increases linearly with at least one of correlation and continuity, cost that increasingly increases with at least one of correlation and continuity, or cost that decreasingly increases with at least one of correlation and continuity.

It is thus an object of at least one embodiment of the invention to permit general-purpose cost functions that may be used in novel imaging applications or when empirical data has not been established.

The different cost functions may include at least one interfacial cost function having a lower dependency on continuity than the other cost functions.

It is thus an object of at least one embodiment of the invention to provide a simple method of managing block matching calculations across tissue boundaries.

The above-mentioned matching process by cost functions may only be applied to pre-selected regions to obtain guidance for subsequent matching processes.

It is thus an object of at least one embodiment of the invention to provide a need-based method of managing the sophistication in the matching processes.

These particular objects and advantages may apply to only some embodiments falling within the claims, and thus do not define the scope of the invention.

BRIEF DESCRIPTION OF THE DRAWINGS

FIG. 3 is a perspective representation of a cost function used in the block matching of FIG. 2 varying linearly with correlation and continuity;

FIG. 4 is a graph along lines of arbitrary constant continuity or constant correlation showing variations of the cost function that may emphasize one of continuity or correlation;

FIG. 5 is a flow chart of the present invention including the step of selecting a cost function;

FIGS. 6-8 are flow chart blocks representing alternative methods of selecting the cost function in the flowchart of FIG. 5;

FIG. 9 is a control display of the present invention allowing selection of cost functions by the proxy of tissue type;

FIG. 10 is a figure similar to that of FIG. 9 allowing the selection of cost functions by image protocol;

FIG. 11 is a simplified B-mode image showing an interface between tissue types where a different cost function may be applied; and FIG. 12 is plot of a line along a B-mode image and an elasticity image showing automatic determination of interface regions and cost functions.

DETAILED DESCRIPTION OF THE PREFERRED EMBODIMENT

Figure 1:
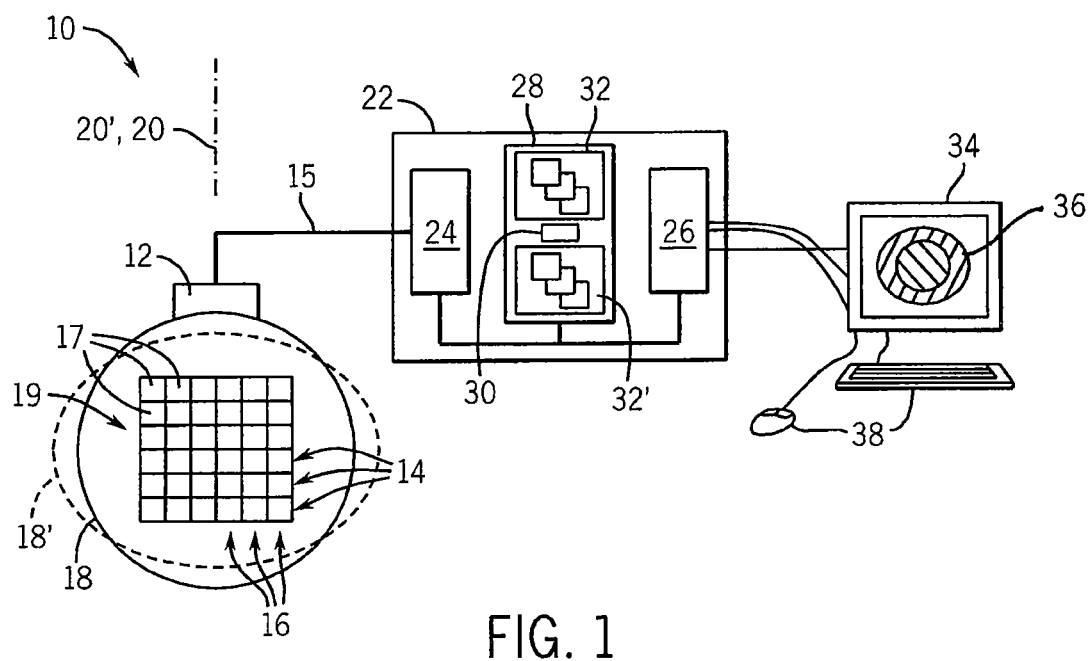
FIG. 1 is a simplified representation of an ultrasound imaging machine suitable for practice of the present invention showing an ultrasonic transducer for collecting rows and columns of ultrasound data and for manually or mechanically deforming the tissue of an object, and showing a multiprocessor computer for processing the ultrasound data according to a stored program to produce an ultrasonic elasticity image on a display device.

Referring now to FIG. 1, an elasticity imaging machine 10 of the present invention includes an ultrasonic array transducer 12 that may transmit and receive ultrasonic signals along a propagation axis 20 to acquire ultrasonic echo data 15 at corresponding volume elements 17 throughout a region of interest 19 in the tissue 18.

The echo data 15, and its corresponding volume elements 17, may both be identified by logical rows 14 and columns 16, wherein the rows 14 are generally echo data 15 or volume elements 17 extending perpendicularly to the propagation axis 20, and the columns 16 are generally echo data 15 or volume elements 17 extending parallel to the propagation axis 20. These terms should be understood generally to describe data acquired through a variety of ultrasonic acquisition geometries including those which provide for fan beams of ultrasound and the like, and therefore not be limited to strictly rectilinear rows and columns.

In addition to transmitting and receiving ultrasonic signals along the propagation axis 20, the transducer 12 may also provide a source of deformation along deformation axis 20' generally aligned with a propagation axis 20 of ultrasound from the transducer 12. Generally, echo data 15 will be obtained with the tissue 18 in a first state of deformation and a second state of deformation (indicated by tissue 18') to provide pre-deformation and post-deformation image sets. It will be understood that characterizations of "pre-deformation" and "post-deformation" are arbitrary and in fact the pre-deformation tissue may be the tissue that is deformed by the transducer 12.

The transducer 12 communicates with a processing unit 22 that both provides waveform data to the transducer 12 used to control the ultrasonic beam and collects the ultrasonic echo signals (radio-frequency data) that form the echo data 15. As is understood in the art, processing unit 22 provides for necessary interface electronics 24 that may sample the ultrasonic echo signals to produce the echo data 15. The interface electronics 24 operate under the control of one or more processors 26 communicating with a memory 28, the latter which may store the echo data 15 identified to rows 14 and columns 16 to form pre-deformation data sets 32 of echo data 15 and post-deformation data sets 32' as will be described.

Generally, the processors 26 may execute a stored program 30 contained in memory 28 as will also be described below. The processors 26 also may communicate with an output screen 34 on which may be displayed a strain image 36 and with a keyboard or other input device 38 for controlling the processing unit 22 and allowing for user input as will be understood to those of skill in the art.

Figure 2:
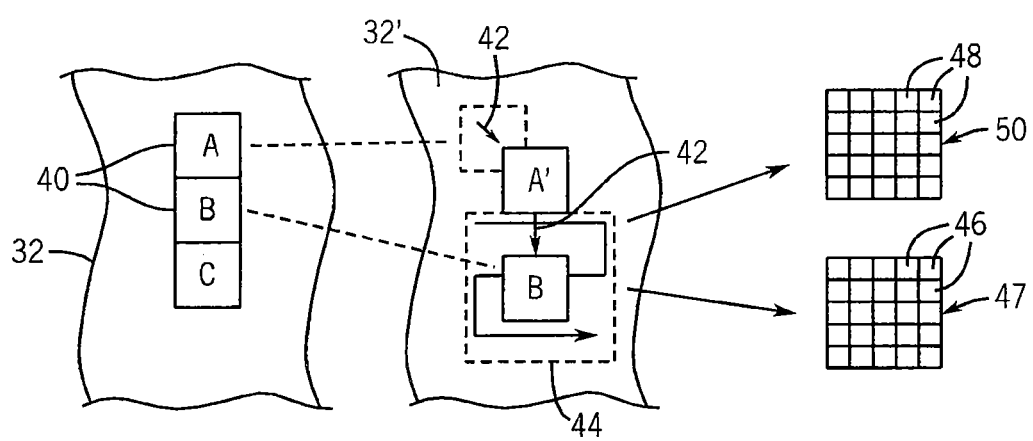
FIG. 2 is a fragmentary representation of selected columns of ultrasound data of a pre-deformation image and a post-deformation image showing a block matching of data of a kernel within a search window to deduce tissue displacement.

Referring now to FIG. 2, the data of the pre-deformation data set 32 may be divided into blocks 40 (e.g. A, B, C) depicted two dimensionally but typically being three-dimensional volumes embracing kernels of multiple points of echo data 15. Each block (for example, block A) in the pre-deformation data set 32 is matched to a corresponding block (for example, A') in the post-deformation data set 32' to deduce a displacement 42 that will be used to calculate elastic parameters.

In the present invention, this block matching involves comparing the block (depicted, for example, using block B) in the pre-deformation data set 32 to corresponding data in a search region/window 44 in the post-deformation data set 32'. In this process, the block B may be thought of as being scanned, for example, in a raster pattern throughout the window 44. At each point in the scan, a correlation value 46 is obtained indicating how well the values of data block B match with the underlying data in the search window 44 at that position. This correlation value 46 is stored in a correlation map 47 relating it to a particular row and column. Correlation is used here to mean any mathematical matching process that yields a match quality, including, for example, computing the sum of the square of the differences between the echo data 15 of corresponding points in the blocks 40 of the pre-deformation data set 32 and post-deformation data set 32'.

At the same time, the displacement 42' between the current scanned position of block B within the search window 44 and the previously deduced block A' and a change in displacement is recorded as a continuity value 48 and stored in a continuity map 50 relating this displacement to a particular row and column of the current scanned position of block B. Generally, the displacement 42 may consider either or both of the length of the vector displacement or the length of the vector displacement and its angle with respect to a previous displacement 42 of block A'. In addition, while the displacement 42 is shown as a simple single vector from block A', it may be the combination of displacement vectors of multiple previously established blocks (for example to the left and right and front and back) so as to provide a measure of deviation of block B from previously established blocks that generally reflects the sense that there is continuity of displacement between adjacent tissue blocks.

Referring now to FIG. 3, in the present invention, the correlation values from correlation map 47 and continuity values from continuity map 50 may serve as arguments input to a cost function 52 yielding a cost value. A cost value may be computed for each correlation value 46 and each continuity value 48 to create a cost matrix 54 equal in size to the continuity map 50 and correlation map 47 and providing a cost value for each row and column of the window 44. The above-mentioned process will be executed for a list of blocks (e.g. A, B and C) to obtain multiple cost matrices for these blocks, respectively. These cost values together produce a cost graph, the local maximum cost-path traveling through the cost graph can be found using computationally-efficient dynamic programming techniques (e.g. Viterbi algorithm, IEEE Trans. Information Theory, 1967). Each node on the minimum cost-path represents the best location of a particular block in terms of trade-offs between correlation and continuity according to the cost function 52. The list of blocks may be chosen along the direction of tissue deformation. Therefore, the directionality of these displacement vectors will make the matching process more robust. For instance, the list of blocks can be chosen along a column 16 of the region of interest 19 to establish guidance for the subsequent motion tracking/matching, as described in U.S. patent application number 2007/0234806 to Jiang et al. published Oct. 11, 2007 and entitled: "Ultrasonic Strain Imaging Device And Method Providing Parallel Displacement Processing" hereby incorporated by reference.

As depicted in FIG. 3, generally the cost provided by the cost function 52 increases with greater (improved) correlation and with greater (improved) continuity. Greater continuity in this sense means smallest changes in displacement 42 and greater correlation means smallest difference between block B and its underlying data.

Referring to FIGS. 3 and 4, the depicted cost function 52 of FIG. 3 depicts a linear relationship between correlation and cost and continuity and cost; however, the present invention contemplates that a family of cost functions 52a, 52b and 52c may be used providing, respectively, functional relationships between cost and either or both of correlation and continuity that decreasingly increase the cost with increasing continuity or correlation (cost function 52a), that linearly increase the cost with increasing continuity or correlation (cost function 52b), or that increasingly increase cost with increasing continuity or correlation (cost function 52c). It will be understood that three cost functions can provide a basic palette of cost functions when specific information about the tissue or imaging protocol is not well characterized. These examples are not intended to limit possible cost functions or to require cost functions that are monotonic as depicted. Within each of these general characterizations of cost functions, there exists a family of cost functions precisely characterizing different curves.

Generally, cost function 52a may be preferred in mapping continuity to cost when there is expected to be significant discontinuity in tissue stiffness (e.g., organ interfaces). Conversely continuity following cost function 52c may be preferred for large homogenous tissue. Cost function 52a may be preferred in mapping correlation to cost for relatively yielding tissue that may produce lower correlation values whereas cost function 52c may be preferred for relatively rigid tissue. These expectations, of course, can be refined and corrected empirically.

Referring now to FIG. 5, the present invention thus requires an ultrasonic echo data acquisition in tissue in two states of deformation as indicated by process block 60 and illustrated schematically in FIG. 1 by tissue 18 and 18'.

At succeeding process block 62, which alternatively could precede process block 60, a cost function is selected for the analysis of this acquired data.

Referring to FIG. 6 in a first embodiment indicated by process block 62a, the cost function may be selected by the user, for example, by inputting a cost function either through a variety of data points or as a mathematical expression, or by selecting from particular cost function shapes depicted schematically. Preferably, however, as shown in FIG. 9, this selection of the cost function is done by a proxy of selecting a particular tissue type or imaging situation. As shown in FIG. 9, this first alternative displays to the user a set of tissue types 64 for which cost functions have been prepared empirically to be useful in these tissue types. Thus, for example, the user may select among abdominal, breast, cranial, thyroid, prostate, uterus or vascular tissue, and an empirically prepared cost function is then used automatically for the calculations.

Alternatively as indicated in FIG. 10, the imaging protocols 65 typically provided in an ultrasound machine and used to adjust other parameters of the ultrasonic acquisition may be used in the additional capacity of selecting the cost function. In this case, the user selects among imaging protocols for abdominal, OB/GYN, breast, vascular, small parts, pediatric, neonatal transcranial, and musculoskeletal. Again, empirically prepared cost functions may be used. One method of preparing cost functions empirically employs phantoms representing these different tissue types or imaging protocols, the phantoms constructed with known materials, and permits modification of the cost function parameters, for example by controlling cost function surface polynomial coefficients, until accurate elasticity images are obtained with minimal artifacts.

Referring now to FIG. 7, an alternative method of defining the cost functions, indicated by process block 62c, uses a B-mode image or other ultrasound-based parametric image of the actual tissue 18. Referring now to FIG. 11, the B-mode image, for example, may show an organ 68 surrounded by other tissue 70. The user may trace a boundary 72 between the organ and surrounding tissue and assign a particular cost function to each. This assignment may, for example, select a cost function from a library of standard cost functions or may use tissue types as proxies as described with respect to FIG. 9. It is expected that it may be desirable to apply a separate cost function to the interstitial regions of the boundary 72, typically one which relaxes the constraints of continuity reflecting the fact of slippage between organs and surrounding tissue.

Referring now to FIGS. 8 and 12, as indicated by process block 62c, the selection of the cost function may also be prepared automatically by analyzing the B-mode image for different tissue types. As shown in FIG. 12 depicting B-mode values taken along line 74 through the organ and tissue of FIG. 11, the echo data 76 of the B-mode image may be analyzed to automatically deduce the boundary 72 (and apply an appropriate cost function to that boundary), for example by looking at abrupt changes in average B-mode values reflecting changes between tissue types or dividing histograms of B-mode data into distinct regions. Morphometric filters may be applied to obtain a three-dimensional boundary around different tissue types. These boundaries and regions may be displayed to the user for correction and/or for the manual selection of cost functions to each region.

Alternatively, the cost functions may be deduced by knowledge of the protocol of the imaging (previously input by the user) indicating the likely types of tissue.

Initial elasticity data 78, for example taken with a standard or default cost function, may also be used in conjunction with the B-mode image data to deduce the correct cost function. Thus, for example, the boundary 72 may be used on the elasticity data 78 to allow analysis of the elasticity statistics in each of regions A (the organ), C (the boundary 72) and B (the surrounding tissue). This initial elasticity measurement, as subdivided, can provide guidance on which cost function to use. For example, as shown in region A, tissue exhibiting fine scale elasticity changes may employ a cost function that relaxes continuity at lower scales. Conversely a tissue showing less variation in elasticity, as shown in region B, may employ a cost function that is more sensitive to changes in continuity.

Referring again to FIG. 5, at process block 80, after the cost function has been selected, a block displacement or similar algorithm is used to find a multipoint displacement between the pre-deformation and post deformation images. In the preferred embodiment this may be done using a Viterbi algorithm of a type known in the art. Such algorithms deduce a likely sequence of states (in this case block displacements) based on previous states and a model of the likelihood of next states, in this case provided by the cost function.

The general organization and path of the block matching may follow the procedure described, for example U.S. patent application number 2007/0234806 to Jiang et al. published Oct. 11, 2007 and entitled: "Ultrasonic Strain Imaging Device And Method Providing Parallel Displacement Processing" hereby incorporated by reference.

As indicated by process block 82, the output of elasticity measurements may then be provided to the user, for example, on the screen 34 of FIG. 1.

It is specifically intended that the present invention not be limited to the embodiments and illustrations contained herein, but include modified forms of those embodiments including portions of the embodiments and combinations of elements of different embodiments as come within the scope of the following claims.

We claim:

1. An ultrasound elasticity imaging machine comprising:
   (a) a transducer assembly producing an axial ultrasonic beam through a region of interest of a material and acquiring an echo signal from that region of interest in a first and second state of deformation;
   (b) an electronic computer configured to provide operator input and output and receiving the echo signals from the transducer assembly and providing data representing multiple first and second tissue regions in the first and second states of deformation, respectively and executing a stored program to:
      (i) select among different cost functions accepting arguments of measures of correlation and measures of continuity, the measures of correlation reflecting a similarity of data of given first and second tissue regions in the first and second states of deformation and the measures of continuity reflecting an amount of displacement of the given first tissue region with respect to another first tissue region in the first and second states of deformation, and functionally combining the measures of correlation and continuity to produce a cost value, the different costs functions providing different contributions of both correlation and continuity in producing the cost value, the selection among different cost function receiving an input from a user indicating at least one of a tissue type and tissue imaging protocol and selecting among the different cost functions dependent on the input;
      (ii) apply the cost function to correlation and continuity values for various matchings of the data of the first and second regions in the first and second states of deformation to produce at least one cost value used in identifying particular matchings between the first and second regions in the first and second states of deformation to deduce displacement of the material under deformation; and
      (iii) output to an operator information revealing elastic parameters of the material based on the deduced displacement.

2. The ultrasonic elasticity imaging machine of claim 1 wherein the electronic computer is configured to receive a cost function selection input from the operator input identifying a tissue type.

3. The ultrasonic elasticity imaging machine of claim 2 wherein the receivable tissue type is selected from the group consisting of breast, liver, cranium, thyroid, prostate, uterus and vasculature.

4. The ultrasonic elasticity imaging machine of claim 1 wherein the electronic computer is configured to receive a cost function selection input by the operator indicating an imaging protocol.

5. The ultrasonic elasticity imaging machine of claim 4 wherein the imaging protocol is selected from the group consisting of abdominal, obstetrics/gynecology (ob/gyn), breast, vascular, small parts, pediatric, neonatal transcranial, and musculoskeletal.

6. An ultrasound elasticity imaging machine comprising:
   (a) a transducer assembly producing an axial ultrasonic beam through a region of interest of a material and acquiring an echo signal from that region of interest in a first and second state of deformation;
   (b) an electronic computer configured to provide operator input and output and receiving the echo signals from the transducer assembly and providing data representing multiple first and second tissue regions in the first and second states of deformation, respectively and executing a stored program to:
  (i) select among different cost functions accepting arguments of measures of correlation and measures of continuity, the measures of correlation reflecting a similarity of data of given first and second tissue regions in the first and second states of deformation and the measures of continuity reflecting an amount of displacement of the given first tissue region with respect to another first tissue region in the first and second states of deformation, and functionally combining the measures of correlation and continuity to produce a cost value, the different costs functions providing different contributions of both correlation and continuity in producing the cost value;
  (ii) apply the cost function to correlation and continuity values for various matchings of the data of the first and second regions in the first and second states of deformation to produce at least one cost value used in identifying particular matchings between the first and second regions in the first and second states of deformation to deduce displacement of the material under deformation; and
  (iii) output to an operator information revealing elastic parameters of the material based on the deduced displacement
wherein the electronic computer is configured to select among cost functions using an analysis of a B-mode or another ultrasound-based parametric image generated from at least one of the echo signals to determine a tissue type.

7. The ultrasonic elasticity imaging machine of claim 6 wherein the electronic computer is configured to select a cost function having reduced emphasis on correlation near boundaries between organs identified from the B-mode image or another ultrasound-based parametric images.

8. The ultrasonic elasticity imaging machine of claim 7 wherein the electronic computer is configured to receive boundaries identified by input from an operator demarcating the boundaries.

9. The ultrasonic elasticity imaging machine of claim 7 wherein the electronic computer is further configured to automatically identify boundaries by image statistics of the B-mode images or the classification of tissue types based on ultrasound signals.

10. The ultrasonic elasticity imaging machine of claim 1 wherein the electronic computer is configured to identify corresponding regions of the echo signals between the first and second states to deduce displacement of the material under deformation using the cost function is applied using dynamic programming techniques.

11. The ultrasonic elasticity imaging machine of claim 1 wherein the electronic computer is further configured to execute the stored program to allow selection among cost functions selected from the group consisting of: cost increasing linearly with at least one of correlation and continuity, cost increasingly increasing with at least one of correlation and continuity, and cost decreasingly increasing with at least one of correlation and continuity.

12. The ultrasonic elasticity imaging machine of claim 1 wherein the electronic computer is further configured to execute the stored program to allow selection among different cost functions including at least one given cost function having a lower dependency on continuity than the other cost functions.

13. A method of making an ultrasonic elasticity image employing an ultrasound elasticity imaging machine comprising:
  (a) a transducer assembly producing an axial ultrasonic beam through a region of interest of a material and acquiring an echo signal from that region of interest in a first and second state of deformation;
  (b) an electronic computer configured to provide operator input and output and receiving the echo signals from the transducer assembly and providing data representing multiple first and second tissue regions in the first and second states of deformation, respectively
the method comprising the steps of executing a stored program to:
  (i) select among different cost functions accepting arguments of measures of correlation and measures of continuity, the measures of correlation reflecting a similarity of data of given first and second tissue regions in the first and second states of deformation and the measures of continuity reflecting an amount of displacement of the given first tissue region with respect to another first tissue region in the first and second states of deformation, and functionally combining the weighted measures of correlation and continuity to produce a cost value, the different costs functions providing different contributions of both correlation and continuity in producing the cost value, the selection among different cost function receiving an input from a user indicating at least one of a tissue type and imaging protocol and selecting a cost function dependent on the input;
  (ii) apply the cost function to correlation and continuity values for various matchings of the data of the first and second regions in the first and second states of deformation to produce at least one cost value used in identifying particular matchings between the first and second regions in the first and second states of deformation to deduce displacement of the material under deformation; and
  (iii) output to an operator information revealing elastic parameters of the material based on the deduced displacement.

14. The method of claim 13 wherein the step of selecting among cost functions uses a B-mode or another ultrasound-based parametric image generated from at least one of the echo signals.

15. The method of claim 14 wherein the cost function is selected to have reduced emphasis on correlation near boundaries between organs identified from the B-mode image.

16. The method of claim 13 wherein the cost function is applied using a Viterbi algorithm employing the cost function.

17. The method of claim 13 wherein the cost functions are selected from the group consisting of: cost increasing linearly with at least one of correlation and continuity, cost increasingly increasing with at least one of correlation and continuity, and cost decreasingly increasing with at least one of correlation and continuity.

18. The method of claim 13 wherein the different cost functions may include at least one given cost function having a lower dependency on continuity than the other cost functions.

* * * * *